United States Patent
Worley

(10) Patent No.: US 8,244,376 B2
(45) Date of Patent: *Aug. 14, 2012

(54) CORONARY SINUS LEAD FOR PACING THE LEFT ATRIUM

(75) Inventor: Seth Worley, Lancaster, PA (US)

(73) Assignee: Oscor Inc., Palm Harbor, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/590,689

(22) Filed: Nov. 12, 2009

(65) Prior Publication Data

US 2010/0137965 A1 Jun. 3, 2010

Related U.S. Application Data

(63) Continuation of application No. 11/144,447, filed on Jun. 3, 2005, now abandoned.

(51) Int. Cl.
*A61N 1/05* (2006.01)
(52) U.S. Cl. .............................. 607/125; 607/9; 607/126
(58) Field of Classification Search .................. 607/125, 607/9, 126
See application file for complete search history.

(56) References Cited

U.S. PATENT DOCUMENTS

| | | | |
|---|---|---|---|
| 4,154,247 A | 5/1979 | O'Neill | |
| 5,215,540 A * | 6/1993 | Anderhub | 604/532 |
| 5,423,865 A | 6/1995 | Bowald et al. | |
| 5,466,254 A | 11/1995 | Helland | |
| 5,476,498 A | 12/1995 | Ayers | |
| 5,683,445 A * | 11/1997 | Swoyer | 607/125 |
| 5,879,295 A | 3/1999 | Li et al. | |
| 5,925,073 A | 7/1999 | Chastain et al. | |
| 5,999,858 A | 12/1999 | Sommer et al. | |
| 6,055,457 A | 4/2000 | Bonner | |
| 6,070,104 A | 5/2000 | Hine et al. | |
| 6,096,036 A * | 8/2000 | Bowe et al. | 606/41 |
| 6,161,029 A | 12/2000 | Spreigl et al. | |
| 6,321,123 B1 | 11/2001 | Morris et al. | |
| 6,363,287 B1 | 3/2002 | Brabec et al. | |
| 6,445,958 B1 | 9/2002 | Machek et al. | |
| 6,584,362 B1 | 6/2003 | Scheiner et al. | |

(Continued)

OTHER PUBLICATIONS

International Search Report From International Application No. PCT/US2006/013439.

*Primary Examiner* — Niketa Patel
*Assistant Examiner* — Alyssa M Alter
(74) *Attorney, Agent, or Firm* — Edwards Wildman Palmer LLP; Scott D. Wofsy; David J. Silvia

(57) ABSTRACT

A method of inserting a pacing lead having a preformed shape into a coronary sinus to pace the left atrium includes providing a lead having an elongated body and proximal and tip sections. The sections are configured such that a first angle less than 90 degrees is defined between the lead body and proximal section and a second angle is defined between the tip and proximal sections. The method further comprises advancing the pacing wire towards the opening of the coronary sinus and advancing the wire into the coronary sinus, such that the first angle is compressed by the coronary sinus opening and a tip electrode included on the tip section contacts the wall of the coronary sinus near the left atrium operably extending the second angle to assure constant contact between the wall of the coronary sinus and the tip electrode.

20 Claims, 7 Drawing Sheets

U.S. PATENT DOCUMENTS

| | | |
|---|---|---|
| 6,647,291 B1 | 11/2003 | Bonner et al. |
| 6,714,823 B1 | 3/2004 | De Lurgio et al. |
| 6,718,211 B2 | 4/2004 | Smits |
| 6,871,085 B2 | 3/2005 | Sommer |
| 6,871,101 B2 | 3/2005 | Zhang et al. |
| 2003/0050681 A1* | 3/2003 | Pianca et al. .................. 607/125 |
| 2003/0208141 A1 | 11/2003 | Worley et al. |
| 2003/0208220 A1 | 11/2003 | Worley et al. |
| 2004/0019359 A1 | 1/2004 | Worley et al. |

* cited by examiner

CORONARY SINUS LEAD FOR PACING THE LEFT ATRIUM

This Application is a continuation application of U.S. Patent application Ser. No. 11/144,447, filed Jun. 3, 2005, which is incorporated herein by reference in its entirety.

FIELD OF THE INVENTION

The present invention relates generally to pacing leads. More particularly, the present invention relates to pacing leads for stable pacing of the left atrium through the coronary sinus.

BACKGROUND OF THE INVENTION

Pacing to the left atrium is important for successful bi-atrial pacing. The pacing to the left atrium is usually accomplished by placing a pacing lead into the coronary sinus, which is a venous structure accessible through the right atrium of the heart and serves to drain the coronary veins. The coronary sinus is generally wider at its ostium and tapers inwardly away from the ostium towards the distal portions of the coronary sinus. The ostium of the coronary sinus is located at the juncture of the right atrium and the right ventricle.

To pace the left atrium, a pacing lead can be positioned so that an electrode contacts the wall of the coronary sinus closest to the left atrium. Because the coronary sinus is in electrical contact with the left atrium, by pacing the coronary sinus at this position, one can also pace the left atrium. The pacing lead generally is advanced to the ostium of the coronary sinus through the right atrium portion of the right heart. For effective pacing, it is desirable that a tip electrode on the pacing lead is placed directly into constant contact with the left atrial side of the coronary sinus. By having this constant contact, high voltages, and thus instability and high thresholds, can be inhibited.

To accomplish such constant contact, different pacing lead configurations have been used to assist in the placement and retention of the pacing lead in the desired position. For example, leads have been used in which a body of the lead is pre-formed to have a sinusoidal or helical configuration enabling the lead to expand into contact with the walls of the coronary sinus and retain the lead. Examples of such pre-formed coronary sinus leads are disclosed in U.S. Pat. No. 5,423,865 to Bowald et al. and U.S. Pat. No. 5,476,498 to Ayers.

Referring to FIGS. 1a-1f, specific examples of pre-formed coronary sinus leads are depicted and described in U.S. Pat. No. 6,321,123 to Morris et al, which is incorporated herein by reference. Pacing leads 20 according to Morris et al. generally comprise a first curved portion 22, a second curved portion 24, a tip electrode 26, and additional electrodes 28. A sheath is used to insert the lead 20 into a coronary sinus. Once the sheath and lead 20 are within the coronary sinus, the sheath is removed and the lead 20 takes its pre-formed shape. The pre-formed "J" in the lead 20 can cause the tip 26 to be pressed up against the wall of the coronary sinus, but only if the width of the pre-formed pacing lead 20 is greater than that of the coronary sinus. When the coronary sinus is wider than the pacing lead 20, the tip electrode can lose contact with the wall of the coronary sinus. This can lead to higher voltage requirements during pacing, and thus higher instability and pacing threshold values.

Referring to FIG. 2, there are also other pacing leads 30 that can be used to pace the left atrium through the coronary sinus, such as the Medtronic Attain® Bipolar OTW Lead Model No. 4194 and leads as disclosed in U.S. Pat. No. 5,683,445 to Swoyer, both of which are incorporated herein by reference. The pacing lead 30 generally includes a first curved portion 32, a second curved portion 34, and a tip electrode 36. As depicted in FIG. 2, the angle 31 at the first curve 32 is greater than ninety degrees. A sheath is used to insert the lead 30 as depicted in FIG. 2 into a coronary sinus. Once the sheath and lead 30 are within the coronary sinus, the sheath is removed and the lead 30 takes its pre-formed shape. This enables the tip electrode 36 to be contact the walls of the coronary sinus. However, using these leads to pace the coronary sinus presents the same problems inherent with the leads according to Morris et al. in that when the coronary sinus is wider than the pacing lead, the tip electrode can lose contact with the wall of the coronary sinus leading to instability and higher pacing voltages and threshold values There is currently a need for a lead assuring stable pacing of the left atrium through the coronary sinus. Because the general problems discussed above have not been addressed by conventional pacing leads, there is a current need for pacing leads addressing the problems and deficiencies inherent with conventional designs.

SUMMARY OF THE INVENTION

The pacing lead of the various embodiments of the present invention substantially addresses the aforementioned problems of conventional designs by providing a lead shape and method of pacing lead deployment that assures that the tip of the lead is firmly in contact with the left atrial side of the coronary sinus. The improved pacing is accomplished because as the lead is advanced into the coronary sinus, the tip electrode is fixed relative to the coronary sinus closest to the left atrium, thus resulting in lower pacing voltages and thresholds and higher pacing stability.

A feature and advantage of embodiments of the invention is that the left atrium can be paced by directing the tip electrode towards the left atrium side of the coronary sinus.

A feature and advantage of embodiments of the invention is that assuring constant contact between the lead electrodes and the walls of the coronary sinus can increase the stability of the pacing.

A feature and advantage of embodiments of the invention is that the design of the pacing lead enables for use on various sized coronary sinuses without sacrificing stability.

A feature and advantage of embodiments of the invention is a method of pacing lead deployment assuring constant contact between the lead electrodes and the walls of the coronary sinus.

DETAILED DESCRIPTION OF THE DRAWINGS

Figure 1A:
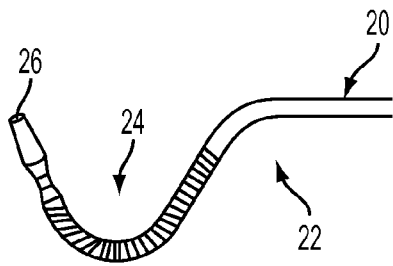
FIG. 1a is a fragmentary elevational view of a prior art coronary sinus pacing lead.
Figure 1B:
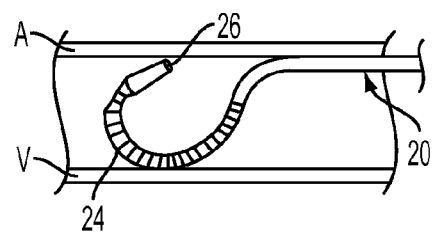
FIGS. 1b-1f are fragmentary cross-sectional views of a coronary sinus depicting prior art coronary sinus pacing leads being inserted into the coronary sinus.
Figure 1C:
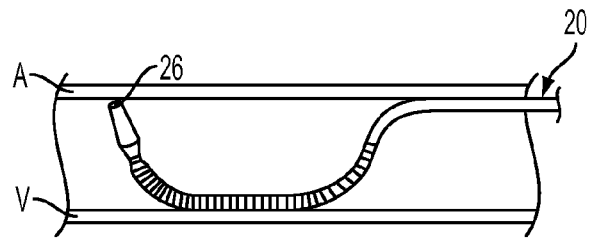
Figure 1D:
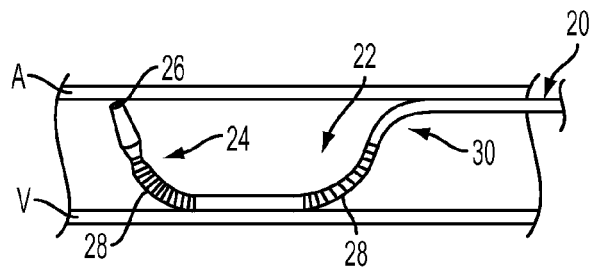
Figure 1E:
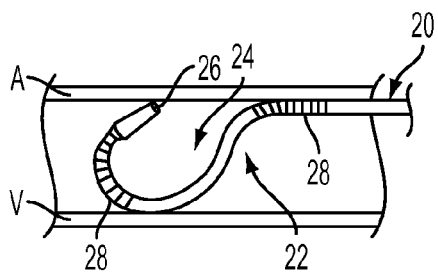
Figure 1F:
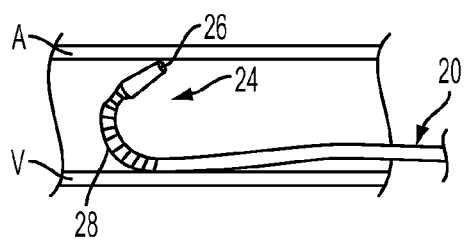
Figure 2:
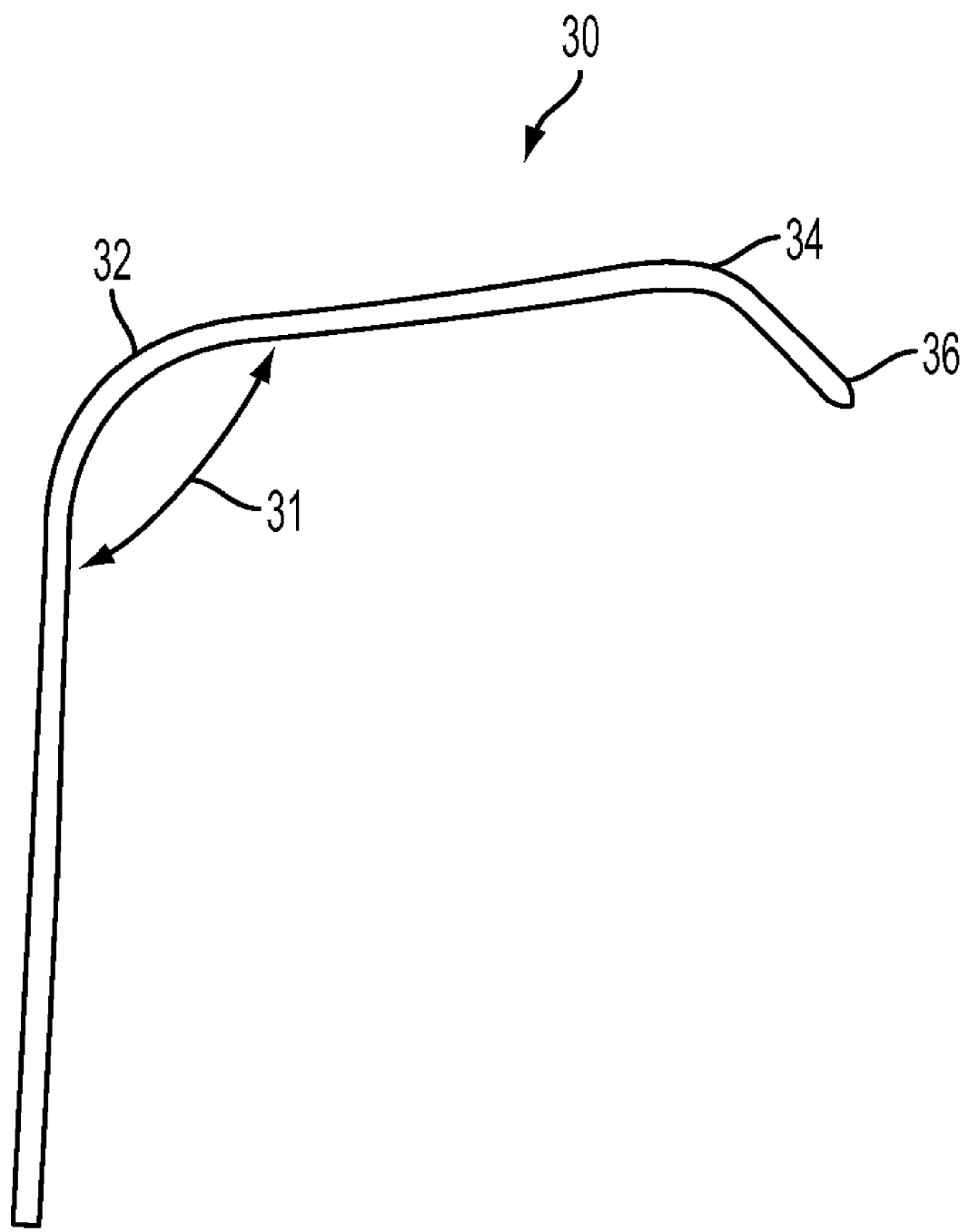
FIG. 2 is a fragmentary elevational view of a prior art left-ventricle pacing lead.
Figure 3:
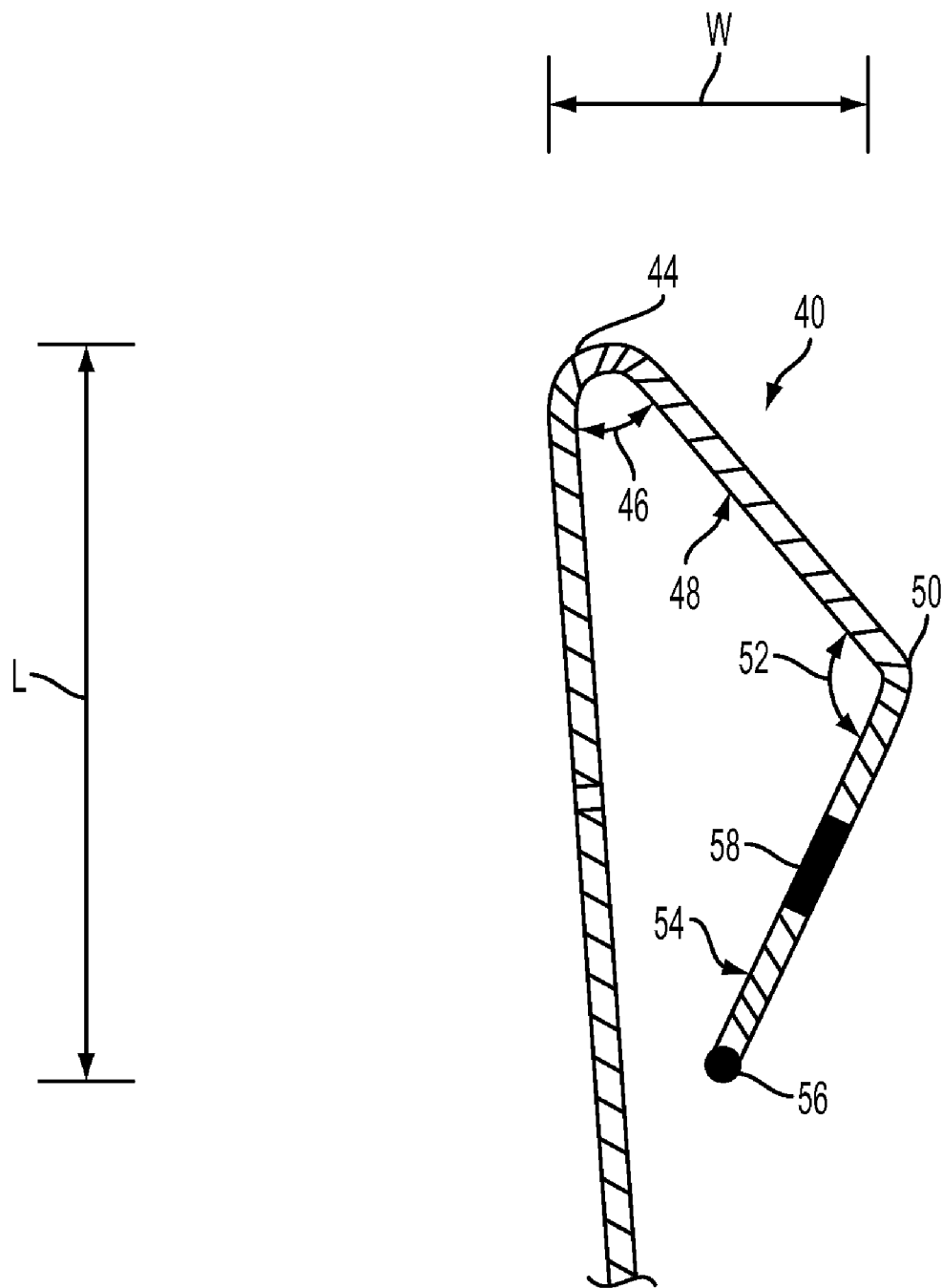
FIG. 3 is a fragmentary elevational view of a coronary sinus pacing lead according to an embodiment of the present invention.

Referring to FIG. 3, a pacing lead 40 according to the various embodiments of the present invention generally includes a main lead portion 42 terminating at a first or proximal curve 44 having a first angle 46, a second or distal curve 50 having a second angle 52, and a tip electrode 56. A first section 48 is generally defined between the first and second curves 44, 50 and a second section 54 is generally defined between the second curve 50 and the tip electrode 56. The pacing lead 40 can also comprise additional curves and sections disposed between the tip electrode and the second curve. Pacing leads are generally known in the art and are disclosed in U.S. Pat. No. 6,321,123 to Morris et al. and U.S. Pat. No. 5,683,445 to Swoyer, both of which are incorporated herein by reference in their entirety.

The pacing lead 40 can also include one or more secondary coil or ring electrodes 58 disposed at any desired point on the main lead portion 42 or first or second sections 48, 54. The pacing lead 40 can further include a stylet 60 to selectively maintain the stiffness of the pacing lead 40 as the lead 40 is advanced into and positioned within the coronary sinus. It will also be appreciated that the shape of tip electrode 56 may be modified as desired, for example by maximizing contact surface area, to enable better contact with the wall of the coronary sinus and resultantly better performance.

The respective lengths of the first and second sections 48, 54 and the first and second angles 46, 52 between the first and second sections 48, 54 of the pacing lead 40 can be selected so that the tip electrode 56 will be in constant contact with the left atrial wall of the coronary sinus, i.e., to maximize contact between the tip electrode 46 and the left atrial wall of the coronary sinus. The overall length L and width W of the first and second sections 48, 54 can also be selected so that the tip electrode 56 will be in constant contact with the left atrial wall of the coronary sinus. The dimensions of the pacing lead according to exemplary embodiments of the present invention can be seen in Table I. Generally, the width of the pacing lead is preferably twice the width of the coronary sinus for stability and good electrical contact.

TABLE I

Pacing lead dimensions according to various exemplary embodiments.

|  | Range | First Exemplary Embodiment | Second Exemplary Embodiment |
| --- | --- | --- | --- |
| Lead Width (French) | 2 F to 9 F | 5 F ± 1 F | 5 F ± 1 F |
| Width - W (mm) | 2.0 to 20.0 | 7.0 ± 5.0 | 7.0 ± 5.0 |
| Length - L (mm) | 5.0 to 60.0 | 30.0 ± 5.0 | 30.0 ± 5.0 |
| First Section (mm) | 2.0 to 30.0 | 10 ± 5.0 | 20.0 ± [10.0 cm] |
| Second Section (mm) | 2.0 to 30.0 | 10 ± 5.0 | 20.0 ± [10.0 cm] |

TABLE I-continued

Pacing lead dimensions according to various exemplary embodiments.

|  | Range | First Exemplary Embodiment | Second Exemplary Embodiment |
| --- | --- | --- | --- |
| First angle* (degrees) | 90-165 | 45 ± 5 | 45 ± 5 |
| Second angle* (degrees) | 105-165 | 120 ± 30 | 120 ± 30 |

*Pre-formed angle prior to insertion into the coronary sinus.

While dimensions of the pacing lead 40 according to exemplary embodiments of the present invention are listed in Table I, one skilled in the art will recognize that changes may be made in form and detail of the dimensions without departing from the spirit and the scope of the invention. Therefore, the exemplary embodiments listed in Table I should be considered in all respects as illustrative and not restrictive.

Figure 4:
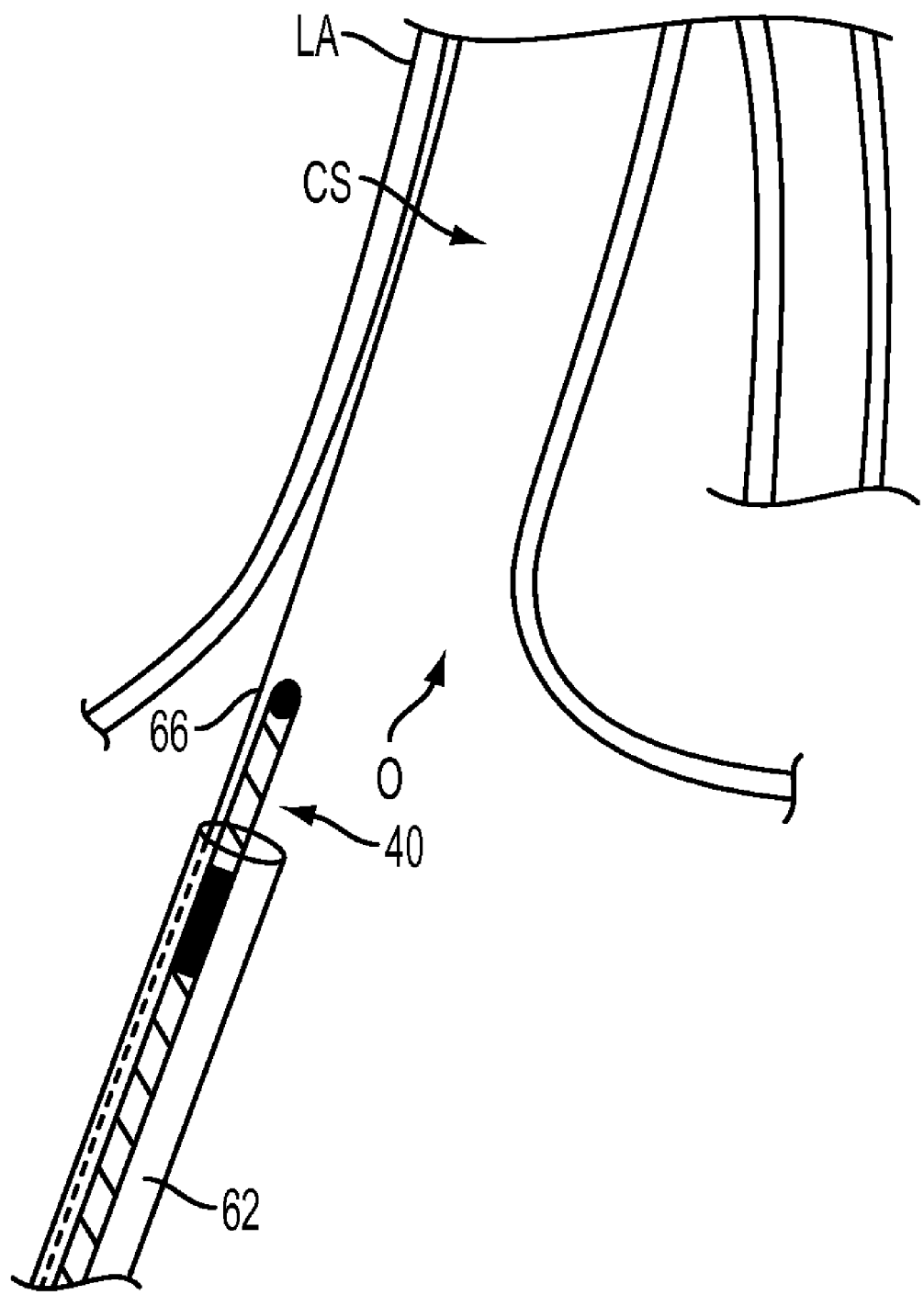
FIG. 4 is a fragmentary cross-sectional view of a coronary sinus depicting a coronary sinus pacing lead according to an embodiment of the present invention prior to being inserted into the coronary sinus.
Figure 5:
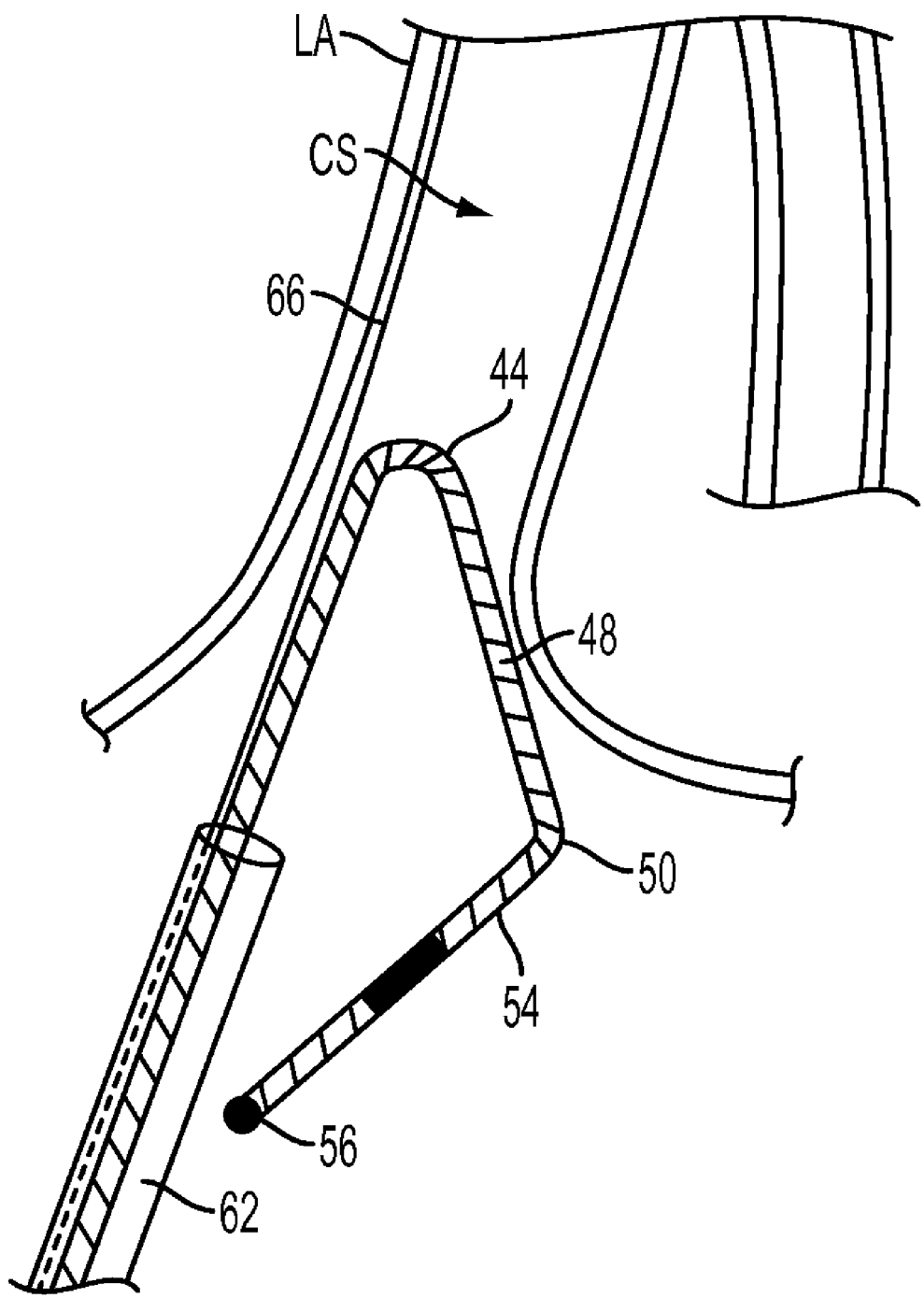
FIG. 5 is a fragmentary cross-sectional view of a coronary sinus depicting a coronary sinus pacing lead according to an embodiment of the present invention being inserted into the coronary sinus.
Figure 6:
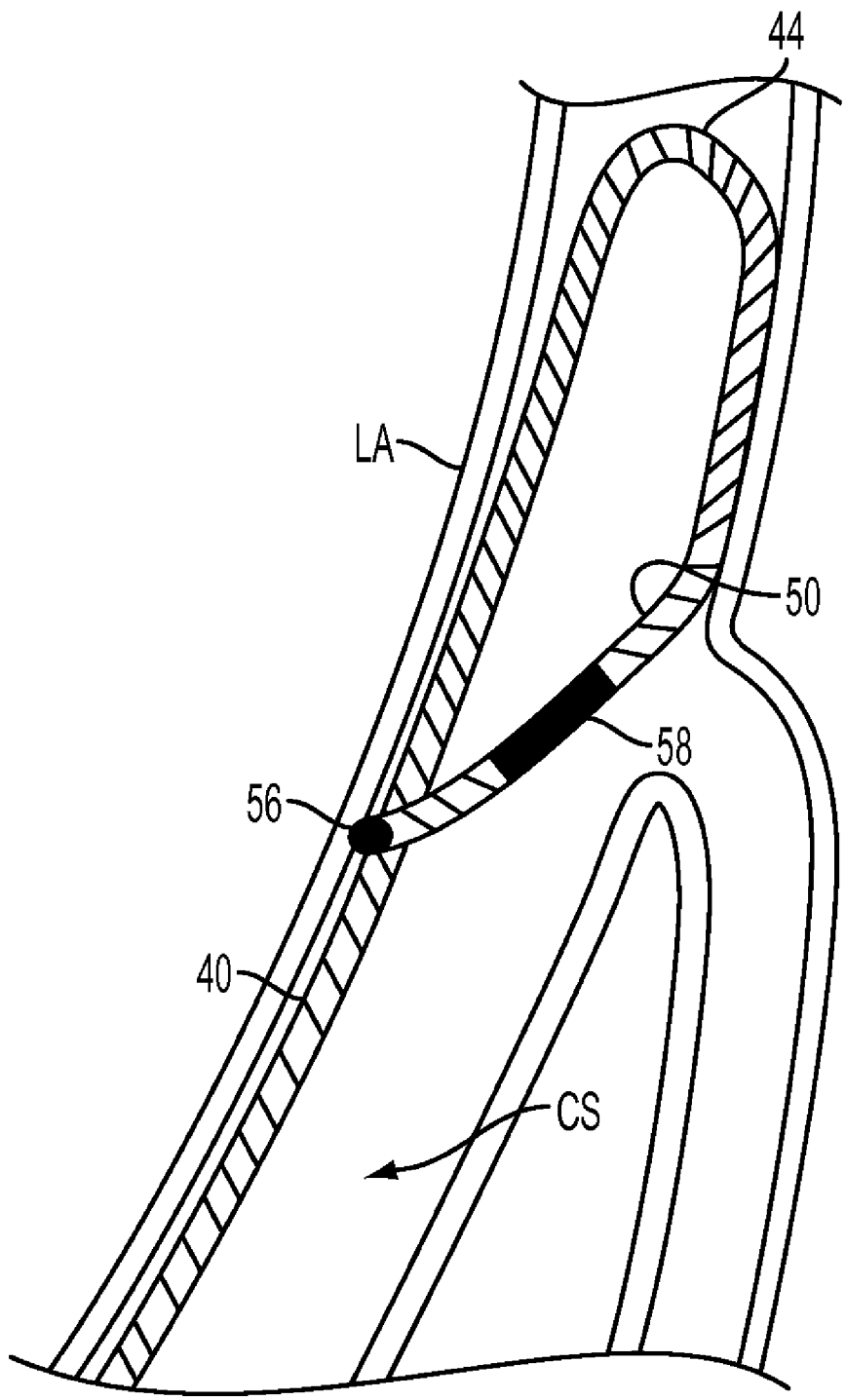
FIG. 6 is a fragmentary cross-sectional view of a coronary sinus depicting a coronary sinus pacing lead according to an embodiment of the present invention inserted into the coronary sinus.

Referring to FIGS. 4-6, implanting the pacing lead 40 into the coronary sinus can be accomplished by first inserting a stylet 60 into the pacing lead 40 and then advancing the pacing lead 40 with stylet 60 towards the ostium of the coronary sinus. Introducers for accessing the coronary sinus of the heart can be seen in U.S. Patent Application Publication Nos. 2003/0208141A1, 2004/0019359A1, and 2003/0208220A1, each to Worley et al., which are incorporated herein by reference. The implantation can be done using a guide wire supported guiding catheter 62 having a sheath 64 and guide support wire 66. A guide wire supported guiding catheter 62 is disclosed, for example, in U.S. Pat. No. 6,714,823, which is incorporated herein by reference. Alternatively, where the coronary sinus is of a smaller diameter, or where it is desired to pace the smaller diameter distal portion of the coronary sinus, pacing lead 40 may be inserted tip first using a sheath and stylet.

To implant the pacing lead 40 using a guiding catheter 62, one end of the guide wire 66 is first inserted deep into the coronary sinus. The other end of the guide wire 66 is operably coupled to the sheath 64 of the guiding catheter 62. The guide wire 66 can then maintain the positioning of the sheath 64 proximate the ostium of the coronary sinus.

Once the sheath 64 is held into place proximate the ostium of the coronary sinus, the stylet 60 of the pacing lead 40 is withdrawn out of the pacing lead 40 to a position proximate the first or proximal bend 44 of the pacing lead 40. The pacing lead 40 can then be advanced out of the sheath 64 while maintaining the stylet 60 at its position proximate the first bend 44 of the lead 40.

After the pacing lead 40 has been advanced out of the sheath 64 so that the lead 40 takes its pre-formed shape, the stylet 60 is kept at the first bend 44 of the pacing lead 40 while the lead 40 and stylet 60 are advanced into the coronary sinus, proximal bend 44 first. As stated above in Table I, in a first embodiment of the present invention, the first angle 46 between the first and second sections 48, 54, in its pre-formed configuration, is approximately 120 degrees.

As the pacing lead 40 is inserted into the ostium of the coronary sinus, the first angle 46 will compress or decrease until the tip electrode 56 comes into contact with the wall of the coronary sinus. Once this happens, the second angle 52 between the first and second sections 48, 54 will increase, e.g., to approximately one hundred and fifty degrees, due to compressive forces placed on the tip 56 as the pacing lead 40 progresses into the narrowing structure of the coronary sinus. In other words, in this wedged position, the walls of the coronary sinus flatten the distal curve 50 as the lead 40 is advanced into the tapering tubular structure of the coronary sinus. The tapering shape of the coronary sinus maximizes the contact between the tip electrode 56 and left atrium side of the coronary sinus.

Figure 7:
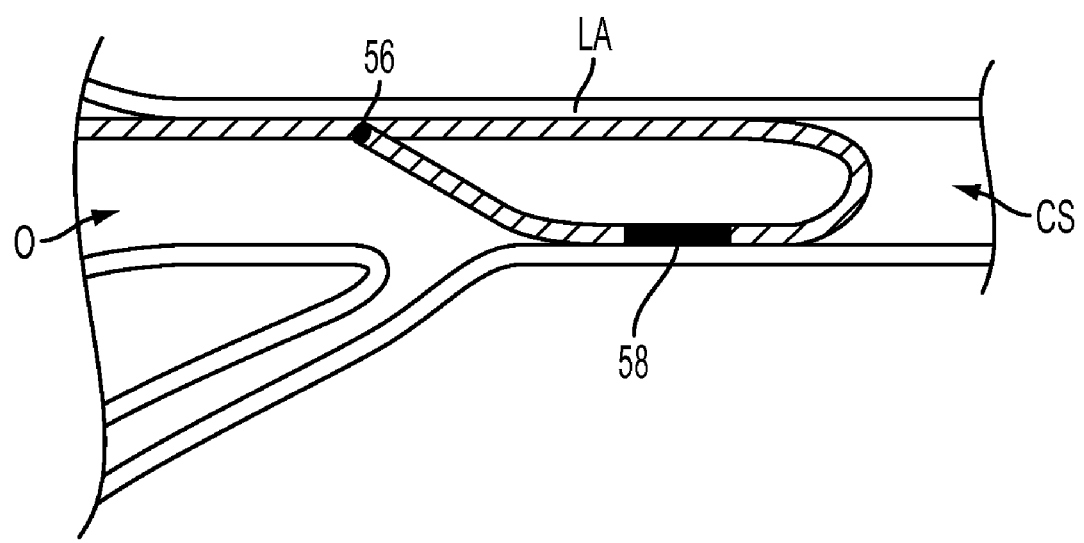
FIG. 7 is a fragmentary cross-sectional view of a coronary sinus depicting a coronary sinus pacing lead according to an embodiment of the present invention inserted into the coronary sinus.

By compressing the proximal and distal curves 44, 50, the lead 40 folds over and the tip electrode 56 is pressed against the left atrial side of the coronary sinus, thus improving the contact between the tip electrode 56 and the wall of the coronary sinus. Contact between the tip electrode 26 and the coronary sinus is maintained as the pacing lead 40 expands to assume its natural, expanded state. The contact results in lower pacing voltages and thresholds and higher pacing stability. The contact also inhibits any movement of the pacing lead 40 due to the heart beating and breathing of the patient once it is in its place within the coronary sinus. In this position, the coil or ring electrode 58 also has improved contact with the wall of the coronary sinus, as depicted in FIG. 7.

While insertion of the pacing lead 40 into the coronary sinus has been depicted and described as being done by first advancing the lead 40 out of the sheath 64 until the lead 40 takes its pre-formed shape, in other embodiments, such as where the coronary sinus has a smaller diameter, the pacing lead 40 can be introduced tip-first in the coronary sinus in the conventional fashion prior to advancing the advancing the lead 40 out of the sheath 64.

Although the present invention has been described with reference to particular embodiments, one skilled in the art will recognize that changes may be made in form and detail without departing from the spirit and the scope of the invention. Therefore, the illustrated embodiments should be considered in all respects as illustrative and not restrictive.

What is claimed is:

1. A pacing lead configured for implantation in a coronary sinus having an opening and a wall defining an interior, the pacing lead comprising:
    a substantially straight elongated lead body defining an elongated longitudinal axis extending from a proximal end of the pacing lead to a first bend defined at a distal end thereof;
    a proximal section extending from the first bend and terminating at a second bend defined at a distal end thereof, such that a first inside angle less than 90 degrees is defined between the lead body and proximal section;
    a tip section having a tip axis extending therethrough and a tip electrode disposed thereon, the tip section extending from the second bend, such that a second inside angle is defined between the tip and proximal sections, wherein the pacing lead is configured such that when at least a portion of the first bend is inserted into the opening of the coronary sinus, the first inside angle is operably compressed by the coronary sinus opening and the tip electrode contacts the wall of the coronary sinus adjacent the lead body whereby the tip axis intersects elongated longitudinal axis of the elongated lead body.

2. The lead of claim 1, further comprising at least one secondary electrode disposed on at least a portion of the lead.

3. The lead of claim 2, wherein the secondary electrode is disposed on the proximal section.

4. The lead of claim 2, wherein the secondary electrode is disposed on the tip section.

5. The lead of claim 1, wherein the first inside angle defined between the lead body and proximal section is less than 45 degrees.

6. The lead of claim 1, wherein the second inside angle defined between the tip and proximal sections is between 90 and 150 degrees.

7. The lead of claim 1, further comprising a stylet disposed therein for selectively maintaining the stiffness of the lead as the lead is inserted into the opening of the coronary sinus.

8. The lead of claim 1, further comprising a catheter and a guidewire operably coupled to the catheter for guiding the lead towards the opening of the coronary sinus.

9. The lead of claim 1, wherein the lead comprises a lead width, the lead width being between 4 and 6 French.

10. A method of inserting a pacing lead having a preformed shape into a coronary sinus to pace a left atrium, the coronary sinus having an opening and a wall defining an interior, the method comprising:
    providing a pacing lead comprising a substantially straight lead body having an elongated longitudinal axis extending from a proximal end of the pacing lead to a first bend defined at a distal end thereof, a proximal section extending from the first bend and terminating at a second bend defined at a distal end thereof, such that a first inside angle less than 90 degrees is defined between the lead body and proximal section, and a tip section having a tip electrode disposed thereon, the tip section having a tip axis extending from the second bend, such that a second angle is defined between the tip and proximal sections;
    advancing the pacing lead towards the coronary sinus opening; and
    advancing the first bend into the coronary sinus, such that the first inside angle is operably compressed by the coronary sinus opening and the pacing lead folds over and the tip electrode contacts the wall of the coronary sinus adjacent the lead body and proximate the left atrium whereby the tip axis intersects the elongated longitudinal axis of the lead body.

11. The method of claim 10, further comprising:
    defining the first inside angle between the lead body and proximal section to be less than 45 degrees; and
    advancing the first curve into the coronary sinus, such that the first inside angle is operably compressed to less than 45 degrees by the wall of the coronary sinus.

12. The method of claim 10, further comprising:
    defining the second inside angle defined between the tip and proximal sections to be between 90 and 150 degrees; and
    advancing the first curve into the coronary sinus, such that the second angle is operably extended to greater than 120 degrees by the wall of the coronary sinus.

13. The method of claim 10, further comprising advancing the first curve into the coronary sinus, such that the tip electrode is in substantially constant contact with the wall of the coronary sinus proximate the left atrium.

14. The method of claim 10, further comprising:
    providing at least one secondary electrode disposed on a portion of the pacing lead; and
    advancing the first curve into the coronary sinus, such that the secondary electrode is in substantially constant contact with at least a portion of the wall of the coronary sinus.

15. The method of claim 10, further comprising:
    providing a guide catheter having a guide wire operably coupled thereto for guiding the pacing wire towards the coronary sinus opening;
    anchoring the guide wire into at least a portion of the coronary sinus;
    providing a stylet and inserting the stylet into the pacing wire having the preformed shape until the pacing wire comprises a substantially linear shape;

inserting the pacing wire having the substantially linear shape into the guide catheter;

advancing the guide catheter and pacing wire to a position proximate the opening of the coronary sinus; and withdrawing the stylet out of the pacing wire to a position proximate the first bend;

advancing the pacing wire out of the sheath towards the opening of the coronary sinus, such that the pacing lead comprises the preformed shape prior to advancing the first curve into the coronary sinus.

16. A pacing lead configured for implantation in a coronary sinus having an opening and a wall defining an interior, the pacing lead comprising:

an elongated lead body having a body axis extending therethrough and a first bend defined thereon;

a proximal section having a second bend defined thereon, the proximal section extending from the first bend and defined between the first and second bends, such that a first inside angle less than 90 degrees is defined between the lead body and proximal section;

a tip section having a tip axis extending therethrough and a tip electrode disposed thereon, the tip section extending from the second bend, such that a second inside angle is defined between the tip and proximal sections, wherein the pacing lead is configured such that when at least a portion of the first bend is inserted into the opening of the coronary sinus, the first inside angle is operably compressed by the coronary sinus opening and the tip electrode contacts the wall of the coronary sinus, wherein when the first bend is inserted into the opening of the coronary sinus, the tip axis intersects the body axis when the tip and body axes are projected onto a common plane parallel to and including the body axis.

17. The lead of claim 16, wherein the first inside angle defined between the lead body and proximal section is less than 45 degrees.

18. The lead of claim 16, wherein the second inside angle defined between the tip and proximal sections is between 90 and 150 degrees.

19. The lead of claim 16, further comprising a stylet disposed therein for selectively maintaining the stiffness of the lead as the lead is inserted into the opening of the coronary sinus.

20. The lead of claim 16, wherein the lead comprises a lead width, the lead width being between 4 and 6 French.

* * * * *